United States Patent [19]

Louiday

[11] Patent Number: 4,769,832
[45] Date of Patent: Sep. 6, 1988

[54] ISOCENTRIC EXAMINATION STAND
[75] Inventor: Andrä E. Louiday, Le Peco, France
[73] Assignee: U.S. Philips Corporation, New York, N.Y.
[21] Appl. No.: 927,783
[22] Filed: Nov. 5, 1986
[30] Foreign Application Priority Data
Nov. 5, 1985 [FR] France ............................. 85 16375
[51] Int. Cl.⁴ ............................................. H05G 1/02
[52] U.S. Cl. .................................. 378/195; 378/193; 378/194; 378/297
[58] Field of Search ................ 378/193, 195, 196, 197, 378/198, 194
[56] References Cited
U.S. PATENT DOCUMENTS
4,150,297 4/1979 Borggren ............................ 378/197
4,481,656 11/1984 Janssen et al. ...................... 378/196
4,646,333 2/1987 Yoshiada et al. ...................... 378/4

FOREIGN PATENT DOCUMENTS
2544191 10/1984 France .
0155937 12/1981 Japan .................................. 378/197

Primary Examiner—Carolyn E. Fields
Assistant Examiner—Joseph A. Hynds
Attorney, Agent, or Firm—Thomas A. Briody

[57] ABSTRACT

An isocentric examination stand for radio-logical examinations of a patient comprising a cradle in the form of an arc of a circle which is circularly displaceable, a cradle support, an X-ray source and a radiation detector, the cradle being composed of mechanically assembled elements forming a structure defining the geometry of the cradle. The structure permits the passage of a supply cable of the source and of the detector into the cradle support.

11 Claims, 2 Drawing Sheets

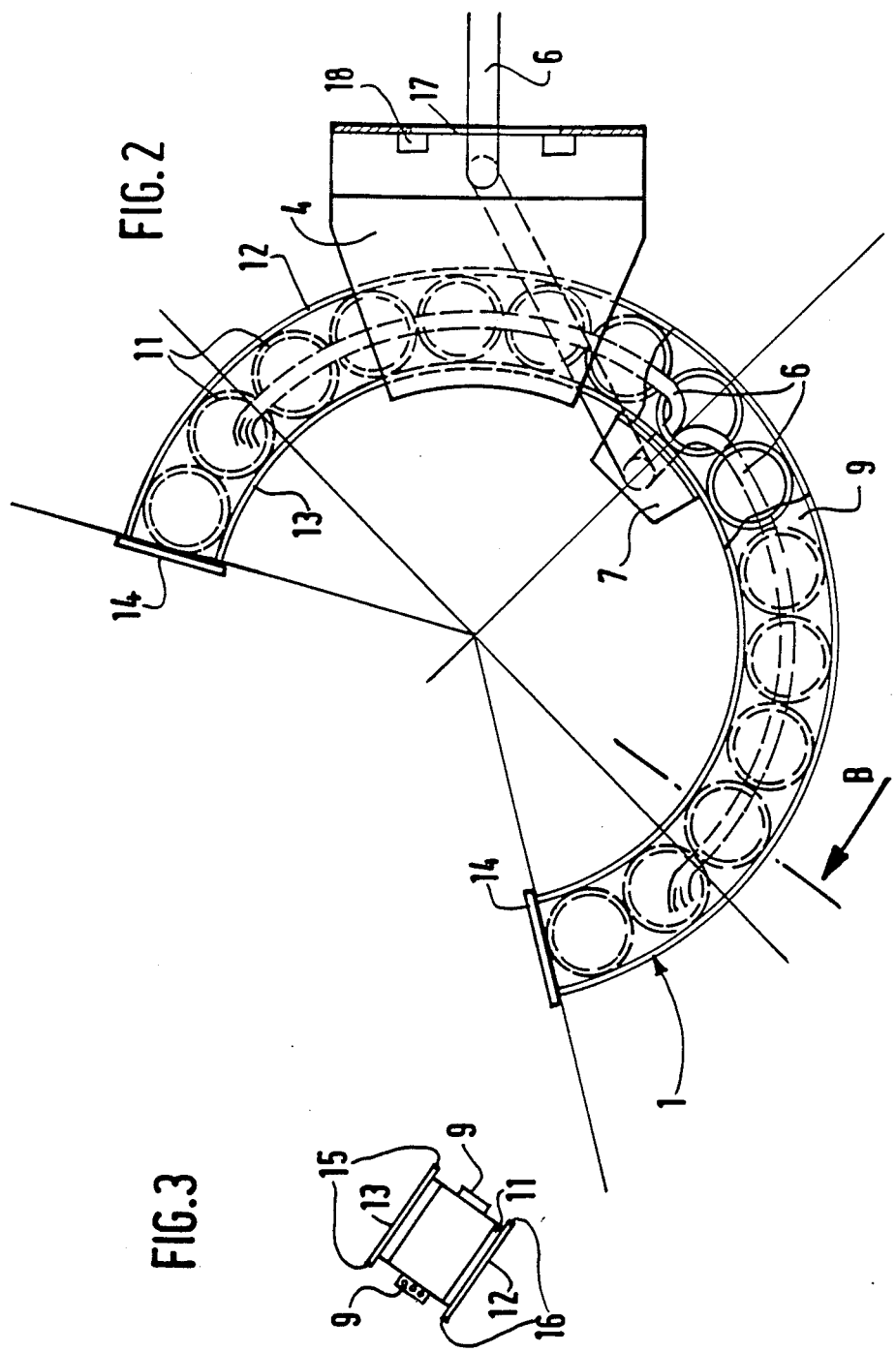

ISOCENTRIC EXAMINATION STAND

BACKGROUND OF THE INVENTION

The invention relates to an isocentric examination stand for radiological examinations of a patient comprising a cradle in the form of an arc of a circle circularly displaceable in a plane containing it about an axis of rotation passing through the centre of the arc of a circle, a cradle support mounted for rotation on an axis parallel to the plane of the cradle and provided with means for circularly displacing the cradle, an X-ray radiation source and a radiation detector both supported by the cradle, disposed on either side of the support, while the axis of source and detector parallel to the plane of the cradle intersects the axis of rotation of the cradle support and a so-called isocentre point Such an examination stand is known from French Pat. No. 2,544,191. French Pat. No. 2,544,191 describes an isocentric examination stand providing for an open cradle displacement conditions which permit lateral incidences and the reconstitution of the initial working axis by replacing on this axis the radiation source and the detector one by the other. These possibilities are obtained by a cradle supported by a movable support in the form of an arc of a circle in turn supported by a socle and circularly displaceable with respect to this socle.

The isocentric examination stands are generally formed from cast or soldered pieces, which are then machined. These pieces have considerable masses of aluminium alloy or of steel in order to ensure that the stands have a considerable mechanical rigidity, whose cradle supports in the out-of-balance-state the weight of the radiation source and of the radiation detector.

The supply cable of the source and of the detector is either suspended from a bracket or incorporated in the cradle and then suspended. Such stands have several disadvantages:

the manufacture of these stands necessarily involves a substantial investment in tools in the case of a moulding or soldering process and an expensive machining of the functional mechanical parts, the supply cable incorporated in the cradle involves a decrease of the mechanical rigidity of the cradle, the cable suspended from a bracket is very voluminous.

SUMMARY OF THE INVENTION

It is an object of the invention to provide an isocentric examination stand of simple and economical design which can be made without complex manufacturing steps.

According to the invention, the isocentric examination stand is characterized in that the cradle is composed of similar juxtaposed elements mechanically connected to each other so as to form a rigid substantially cylindrical structure on which bear at least one external envelope and an internal envelope forming with the structure a cylinder portion, the structure permitting of fixing the supply cable of the source and the X-ray detector and of securing it to the cradle support.

The form of the cradle is predetermined by an assembly of elements connected to each other, for example by screws and nuts or rivets, these elements together constituting a preform. The two envelopes and the supply cable of the source and of the X-ray detector are fixed on this preform, the passage of the cable not adversely affecting the mechanical rigidity of the cradle.

In a preferred embodiment of the invention, the similar elements are portions of a cylindrical tube whose longitudinal axes are parallel to the axis of rotation of the cradle. These elements may also form, for example, regular polygons or may have any other form, which elements when juxtaposed and connected to each other, will form a cradle.

More particularly the internal and external envelopes are ach constituted by a rolled rectangular plate projecting on either side from the similar juxtaposed elements. The preform constituted with the elements connected to each other permits of carrying and of forming internally and externally a strip of sheet iron which takes the form of the geometric envelope of the preform.

Moreover, the longitudinal edges of the internal and external envelopes are rolling strips for guiding the cradle in the cradle support. The rolled sheet iron strips having a width exceeding the length of the cylindrical tubes constituting, for example the preform project laterally on either side from the said tubes so as to form a cradle of H-shaped cross-section, the limbs of the H constituting the rolling strips which guide the cradle in its plane of displacement about its axis of rotation.

In another particular embodiment of the invention, the supply cable of the source and of the X-ray detector fixed on the juxtaposed elements traverses the cradle so as to leave it at a zone dividing the said cradle into two equal arcs and to enter the cradle support whilst forming a ring. The passage of the cable through the medial part of the cradle permits the latter of being displaced whilst extremely rotating in its plane by reducing to a maximum the length of the cable forming the ring.

Preferably, the cradle support is mounted for rotation on a circular rolling track forming a crown. The supply cable, which penetrates into the cradle support, leaves it at the axis of rotation of the support through an open passage centred at the axis of the crown or connection to the fixed sources of supply.

BRIEF DESCRIPTION OF THE DRAWINGS

In order that the invention may be readily carried into effect, it will now be described more fully, by way of example, with reference to the accompanying drawings, in which:

FIG. 2 is a side view in the direction of the arrow A of FIG. 1, with the cradle 1 partly cut away FIG. 3 is a straight sectional view along the arrow B of FIG. 2 of the cradle.

DESCRIPTION OF THE PREFERRED EMBODIMENTS

Figure 1:
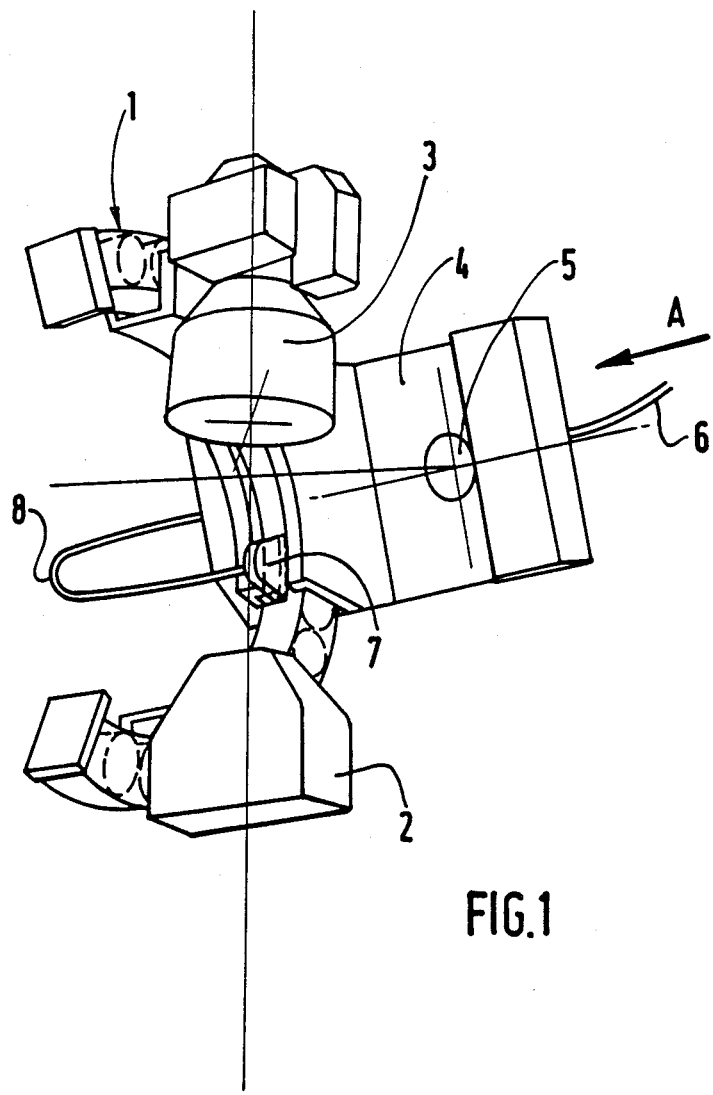
FIG. 1 is a perspective view of the assembly of an isocentric examination stand.

FIG. 1 is a perspective view of the assembly of an isocentric examination stand comprising a cradle 1 on which a source 2 of X-ray radiation and an X-ray radiation detector 3, such as, for example, an image intensifier tube, are mounted diametrically opposite to each other. The cradle 1 is carried by a cradle support 4 mounted for rotation about a horizontal axis 5 contained in the plane by an axis of source 2 and detector 3 parallel to the plane of rotation of the cradle and which is displaced circularly, like this cradle. The intersection of the axis 5 and of the axis of source and detector is a point designated at isocentre.

An electrical supply cable 6 of the source 2 and of the detector 3 is fixed by a bracket 7 and forms a ring 8 before it penetrates into the cradle support 4.

FIG. 2 is a side view in the direction of the arrow A (FIG. 1) of the stand in which the source 2, the detector 3 and partly a cable cladding 9 have been omitted so that the path traversed by the supply cable 6 of the X-ray source and of the detector can be seen.

The cradle (seen partly cut away) is composed of cylinder portions 11 (rigid cells) shown in an end view in the Figure and each forming two concentric circles. The cylinders are connected to each other by mechanical elements not shown in the drawing, which may be, for example, screws and nuts or rivets, the cylinders having been preperforated with a high degree of precision in order that, by connecting the cylinders to each other, the perforation and mounting realize and impose on each of the cylinders 11 a position defining mutually with accuracy a structure having roughly the form of a cradle.

The structure then formed with the assembly of the cylinders 11 carries at least one external envelope 12 and at least one internal envelope 13, which are preperforated and bear on generatrices of the cylinders 11 so as to form a cradle representing perfectly a hollow cylinder having predetermind calibrated dimensions. The open cradle forms a cylindrical sector of 240° in order that the source 2 and the detector 3 can be positioned diametrically opposite to each other. Two flanges 14 close the two end sections of the cylindrical sector.

The form of the cradle thus obtained requires only a precise perforation without moulding or soldering, while the rolling tracks are obtained directly with the internal envelope 13 and the external envelope 12.

The cradle 1 is mounted on a cradle support 4, in which it slides over disks for its circular displacement, the disks, whose axis of rotation is parallel to the axis of rotation of the cradle, pinching the two projecting lateral edges 15, 16 of each of the two envelopes 12 and 13.

The cable 6 is disposed and fixed whilst bearing on the structure formed by the cylinders 11 and then covered by a cladding 9 closing the cylindrical cradle sections. The cable arrives at a bracket 7 mounted on the internal envelope 13 and disposed so as to divide the cradle into two substantially equal arcs. Only one passage hole is formed on the internal envelopes, the passage of the cable thus obtained not adversely affecting the mechanical rigidity of the cradle.

When the bracket 7 is placed in a medial zone of the cradle, the cable leaving the cradle and penetrating into the cradle support 4 forms a ring of minimum length, the length of the ring being connected with the distance between the bracket 7 and the support 4 when the displacement of the cradle is extreme.

The passage of the cable 6 into the cradle support 4 connected with the construction of the cradle 1 and with the position of the bracket 7 imposes the requirement that the cable can leave again in the direction of the electric energy sources (high voltage, sector). In the embodiment according to the invention, the cable 6 passed into the cradle support 4 is passed into a hole 17 provided in the middle of a rolling track 18 in the form of a crown. The rolling track 18 is, for example, a cirucular axis of rotation provided with disks defining the axis of rotation 5 of the cradle support 4.

FIG. 3 is a sectional view of the cradle along the arrow B showing a cylinder 11 in longitudinal sectional view, the internal envelope 13 and the external envelope 12 bearing on a generatrix of the cylinder and projecting at the two ends of the cylinder so as to form rolling strips, as well as two flanges 9 enclosing the supply cable 6 of the X-ray radiation source and of the detector.

I claim:

1. An isocentric examination stand for radiological examinations of a patient comprising
   a cradle in the form of an arc of a circle circularly displaceably in a plane containing it about an axis of rotation passing through the centre of the arc of a circle,
   a cradle support mounted for rotation on an axis parallel to the plane of the cradle and provided with means for circularly displacing the cradle,
   an X-ray radiation source and a radiation detector both supported by the cradle and disposed on opposite positions of the support, while the axis of source and detector parallel to the plane of the cradle intersects the axis of rotation of the cradle support isocentre point,
   characterized in that the cradle comprises a plurality of similar juxtaposed elements mechanically connected to each other in a line so as to form a rigid substantially cylindrical structure on which bear at least one external envelope and one internal envelope forming with the structure a cylinder portion, the structure comprising means for permitting the fixing of a supply cable of the source and the radiation detector and of securing it to the cradle support.

2. A stand as claimed in claim 1, characterized in that the similar elements are portions of a cylindrical tube whose longitudinal axes are parallel to the axis of rotation of the cradle.

3. A stand as claimed in claim 1, characterized in that the internal and external envelopes are each constituted by a rolled rectangular plate projecting on either side from the similar juxtaposed elements.

4. A stand as claimed in claims 1 or 3, characterized in that the projecting longitudinal edges of the internal and external envelopes are rolling strips for guiding the cradle in the cradle support.

5. A stand as claimed in claim 1, characterized in that the supply cable of the source and of the detector fixed on the juxtaposed elements traverses the cradle and then leaves it at a zone dividing the said cradle into two equal arcs and enters the cradle support whilst forming a ring.

6. A stand as claimed in claim 1, characterized in that the cradle support is mounted for rotation on a circular rolling track forming a crown.

7. An isocentric examination stand comprising:
   a cradle support;
   a cradle having the form of an arc, said cradle being mounted on the cradle support for rotation around an axis which is transverse to the arc;
   a radiation source arranged on the cradle at a first position; and
   a radiation detector arranged on the cradle at a second position opposite the first position;
   characterized in that the cradle comprises a plurality of substantially identical non-rotatable rigid cells fastened to each other in a line along the arc of the cradle;

said cradle further comprising an internal envelope fastened to the line of cells on the inside of the arc; and an external envelope fastened to the line of cells on the outside of the arc.

8. An isocentric examination stand as claimed in claim 7, characterized in that the rigid cells are hollow.

9. An isocentric examination stand as claimed in claim 8, characterized in that:
- the cradle has the form of an arc of a circle, said circle being situated in a plane, said circle having a center, said arc having an inside facing the center of the circle and having an outside facing away from the center of the circle;
- the cradle is mounted on the cradle support for rotation around an axis which passes through the center of the circle and which is perpendicular to the plane of the circle; and
- the radiation detector is arranged on the cradle at a second position opposite the first position such that a line from the source to the detector intersects the axis of rotation of the cradle.

10. An isocentric examination stand as claimed in claim 9, characterized in that:
- each rigid cell comprises a segment of a cylindrical tube having at least one side wall and a longitudinal axis extending parallel to the side wall;
- the rigid cells are fastened to each other at their side walls; and
- the longitudinal axes of the rigid cells are parallel to the axis of rotation of the cradle.

11. An isocentric examination stand as claimed in claim 10, characterized in that:
- each rigid cell has a length in the direction of its longitudinal axis and has ends through which the longitudinal axis passes;
- the arc has a circumference; and
- each envelope comprises a curved rectangular plate having a length extending along the circumference of the arc and having a width extending parallel to the longitudinal axis of the rigid cells, the width of each envelope exceeding the length of each rigid cell such that each rigid envelope projects beyond both ends of the rigid cells.

* * * * *